(12) United States Patent
Yoshikawa et al.

(10) Patent No.: US 9,493,912 B2
(45) Date of Patent: Nov. 15, 2016

(54) METHOD FOR PRODUCING LIGNIN DEGRADATION PRODUCT

(71) Applicant: KAO CORPORATION, Tokyo (JP)

(72) Inventors: Hayato Yoshikawa, Wakayama (JP); Yuuji Maruno, Wakayama (JP)

(73) Assignee: KAO CORPORATION, Tokyo (JP)

( * ) Notice: Subject to any disclaimer, the term of this patent is extended or adjusted under 35 U.S.C. 154(b) by 200 days.

(21) Appl. No.: 14/367,054

(22) PCT Filed: Dec. 4, 2012

(86) PCT No.: PCT/JP2012/081421
§ 371 (c)(1),
(2) Date: Jun. 19, 2014

(87) PCT Pub. No.: WO2013/094398
PCT Pub. Date: Jun. 27, 2013

(65) Prior Publication Data
US 2015/0041083 A1    Feb. 12, 2015

(30) Foreign Application Priority Data

Dec. 20, 2011 (JP) ................................. 2011-278202
Apr. 27, 2012 (JP) ................................. 2012-102972
Nov. 27, 2012 (JP) ................................. 2012-258389

(51) Int. Cl.
| | |
|---|---|
| D21H 17/25 | (2006.01) |
| C07G 1/00 | (2011.01) |
| C12P 19/14 | (2006.01) |
| C08H 7/00 | (2011.01) |
| D21B 1/30 | (2006.01) |
| D21H 17/00 | (2006.01) |
| D21H 17/06 | (2006.01) |
| C08H 8/00 | (2010.01) |
| C08L 97/00 | (2006.01) |

(52) U.S. Cl.
CPC ............... *D21H 17/25* (2013.01); *C07G 1/00* (2013.01); *C08H 6/00* (2013.01); *C08H 8/00* (2013.01); *C08L 97/005* (2013.01); *C12P 19/14* (2013.01); *D21B 1/303* (2013.01); *D21H 17/005* (2013.01); *D21H 17/06* (2013.01)

(58) Field of Classification Search
CPC ....................................................... C07G 1/00
See application file for complete search history.

(56) References Cited

U.S. PATENT DOCUMENTS

| | | |
|---|---|---|
| 4,742,814 A | 5/1988 | Sinner et al. |
| 2008/0299629 A1 | 12/2008 | Hallberg et al. |
| 2010/0121110 A1 | 5/2010 | Voitl et al. |
| 2010/0159516 A1 | 6/2010 | Diner et al. |
| 2010/0249390 A1 | 9/2010 | Azuma et al. |

FOREIGN PATENT DOCUMENTS

| | | |
|---|---|---|
| CN | 101684480 A | 3/2010 |
| JP | 62-111700 A | 5/1987 |
| JP | 2004-190150 A | 7/2004 |
| JP | 2008-5832 A | 1/2008 |
| JP | 2009-114181 A | 5/2009 |
| JP | 2010-520157 A | 6/2010 |
| JP | 2011-10617 A | 1/2011 |
| JP | 2011-92151 A | 5/2011 |
| WO | WO 2008/017145 A1 | 2/2008 |

OTHER PUBLICATIONS

Araque et al. Enzyme and Microbial Technology, 2008, 43:214-219.*
Ramos et al. J. Agric. Food Chem., 2001, 49:1180-1186.*
Office Action issued in the corresponding Chinese Patent Application No. 201280062614.1 on Nov. 3, 2015.
Extended European Search Report, dated May 26, 2015, for European Application No. 12859442.1.
International Search Report (Form PCT/ISA/210) for International Application No. PCT/JP2012/081421, dated Feb. 12, 2013, with an English translation.
Zhao et al., "Organosolv pretreatment of lignocellulosic biomass for enzymatic hydrolysis," Applied Microbiology and Biotechnology, vol. 82, 2009 (Published online Feb. 12, 2009), pp. 815-827.

* cited by examiner

*Primary Examiner* — Bin Shen
(74) *Attorney, Agent, or Firm* — Birch, Stewart, Kolasch & Birch, LLP

(57) ABSTRACT

The present invention relates to [1] a process for producing a lignin degradation product, including the following steps (1) to (3), and [2] a lignin degradation product produced by the process as described in the above [1]: Step (1): subjecting a lignocellulose raw material to enzymatic saccharification treatment to obtain a saccharification residue; Step (2): subjecting the saccharification residue obtained in the step (1) to heat treatment in a mixed solvent containing water and an organic solvent having a solubility in 20° C. water of not less than 90 g/L to obtain a heat treatment solution containing the lignin degradation product; and Step (3): subjecting the heat treatment solution obtained in the step (2) to solid-liquid separation to remove insoluble components from the heat treatment solution, thereby obtaining the lignin degradation product. The present invention provides a process for producing a novel lignin degradation product having a low degree of denaturation, a high solubility in solvents and a high versatility with a high yield.

19 Claims, No Drawings

METHOD FOR PRODUCING LIGNIN DEGRADATION PRODUCT

FIELD OF THE INVENTION

The present invention relates to a process for producing a lignin degradation product having a low degree of denaturation, a high solubility in solvents and a high versatility.

BACKGROUND OF THE INVENTION

Lignins are aromatic polymers contained in many plants including trees or gramineous plants, and are contained together with celluloses and hemicelluloses in these plants. The above three components are present as a lignocellulose in which the components are complicatedly bonded to each other, in a cell wall of the plants. Therefore, it is not easy to separate the lignocellulose into these components. Also, lignins have a higher reactivity than that of the celluloses and are therefore readily susceptible to condensation reaction upon heating, and finally transformed into a massive substance that is inert and has a poor solubility in solvents.

As the method of separating lignins from the lignocellulose raw material with a high yield, there is known a Kraft cooking method used mainly by paper-making companies (for example, refer to Patent Document 1). Also, studies have been made on a method of disentangling celluloses and lignins from each other by treating the lignocellulose with hydrogen peroxide as an oxidizing agent (for example, refer to Patent Document 2) or by immersing the lignocellulose in an organic solvent under high-temperature and high-pressure conditions (for example, refer to Patent Document 3). In addition, studies have also been made on a method of removing polysaccharides from the lignocellulose raw material using an enzyme to utilize the resulting enzymatic saccharification residue (for example, refer to Patent Document 4).

CITATION LIST

Patent Literatures

Patent Document 1: JP 2004-190150A
Patent Document 2: JP 2009-114181A
Patent Document 3: JP 62-111700A
Patent Document 4: JP 2011-92151A

SUMMARY OF THE INVENTION

The present invention relates to the following aspects [1] and [2].
[1] A Process for Producing a Lignin Degradation Product, Including the Following Steps (1) to (3):
  Step (1): subjecting a lignocellulose raw material to enzymatic saccharification treatment to obtain a saccharification residue;
  Step (2): subjecting the saccharification residue obtained in the step (1) to heat treatment in a mixed solvent containing water and an organic solvent having a solubility in 20° C. water of not less than 90 g/L to obtain a heat treatment solution containing the lignin degradation product; and
  Step (3): subjecting the heat treatment solution obtained in the step (2) to solid-liquid separation to remove insoluble components from the heat treatment solution, thereby obtaining the lignin degradation product.
[2] a Lignin Degradation Product Produced by the Process as Described in the Above Aspect [1].

DETAILED DESCRIPTION OF THE INVENTION

In the Kraft cooking method described in Patent Document 1, when heated in a mixed solution containing sodium hydroxide or sodium sulfite, lignin tends to suffer from significant chemical denaturation. For this reason, in the method of Patent Document 1, it will be difficult to extract lignin present in plants as such, which results in limitation to use of lignin in specific applications and is therefore undesirable from the viewpoint of effective utilization of biomass.

Also, in the method described in Patent Document 2, since a large amount of hydrogen peroxide is treated under a high-temperature condition, lignin tends to suffer from promoted overdegradation and denaturation. As a result, the overdegradation product tends to be hardly separated from a sugar solution, and the denaturation product tends to remains in pulps.

In the method described in Patent Document 3, it may be difficult to fully disentangle the lignin, cellulose and hemicellulose from each other.

In the method described in Patent Document 4, cellulose and hemicellulose still remain in the obtained solid component containing lignin, and the solid component is insoluble in water or an organic solvent, so that it may be difficult to use the lignin as a high-molecular aromatic polymer, and further modify and functionalize the lignin.

In consequence, the present invention aims at providing a process for producing a lignin degradation product having a low degree of denaturation, a high solubility in solvents and a high versatility with a high yield.

The present inventors have found that when subjecting a lignocellulose raw material to enzymatic saccharification and treating the resulting saccharification residue under specific conditions, it is possible to solve the above conventional problems. The present invention has been accomplished by the above finding.

That is, the present invention relates to the following aspects [1] and [2].
[1] A Process for Producing a Lignin Degradation Product, Including the Following Steps (1) to (3):
  Step (1): subjecting a lignocellulose raw material to enzymatic saccharification treatment to obtain a saccharification residue;
  Step (2): subjecting the saccharification residue obtained in the step (1) to heat treatment in a mixed solvent containing water and an organic solvent having a solubility in 20° C. water of not less than 90 g/L to obtain a heat treatment solution containing the lignin degradation product; and
  Step (3): subjecting the heat treatment solution obtained in the step (2) to solid-liquid separation to remove insoluble components from the heat treatment solution, thereby obtaining the lignin degradation product.
[2] a Lignin Degradation Product Produced by the Process as Described in the Above Aspect [1].

According to the production process of the present invention, it is possible to produce a lignin degradation product having a low degree of denaturation and a high solubility in solvents from a lignocellulose raw material with a high yield. The lignin degradation product obtained by the production process of the present invention exhibits a low degree of denaturation and a high solubility in solvents and therefore can be advantageously subjected to conversion into low-molecular aromatic compounds as well as chemical modification and derivatization according to the aimed applications thereof.

[Process for Producing Lignin Degradation Product]

The process for producing a lignin degradation product according to the present invention includes the following steps (1) to (3):

Step (1): subjecting a lignocellulose raw material to enzymatic saccharification treatment to obtain a saccharification residue;

Step (2): subjecting the saccharification residue obtained in the step (1) to heat treatment in a mixed solvent containing water and an organic solvent having a solubility in 20° C. water of not less than 90 g/L to obtain a heat treatment solution containing the lignin degradation product; and Step (3): subjecting the heat treatment solution obtained in the step (2) to solid-liquid separation to remove insoluble components from the heat treatment solution, thereby obtaining the lignin degradation product.

The reason why the lignin degradation product having a low degree of denaturation, a high solubility in solvents and a high versatility can be produced with a high yield according to the production process of the present invention, is considered as follows, though it is not clearly determined.

That is, in the above step (1), when subjecting the lignocellulose raw material to enzymatic saccharification, polysaccharides contained therein undergo degradation to loosen entanglement between lignin and the polysaccharides, so that it is possible to obtain a saccharification residue that is considerably improved in a degree of freedom of the lignin. Next, in the above step (2), the resulting saccharification residue is immersed in a solvent having a high affinity to the lignin, so that the lignin is swelled and water molecules in the solvent are infiltrated even up to an inside of molecules of the lignin. When heated in this state, the lignin is cut without condensation of lignin molecules under relatively moderate conditions in which the lignin is unsusceptible to denaturation, whereby it is possible to produce a lignin degradation product having a good solubility in solvents and a low degree of denaturation with a high yield.

[Step (1)]

In the step (1), the lignocellulose raw material is subjected to enzymatic saccharification treatment to obtain a saccharification residue.

(Lignocellulose Raw Material)

The lignocellulose raw material used in the step (1) means a plant-based biomass containing cellulose, hemicellulose and lignin.

Examples of the lignocellulose raw material include various timbers such as various wood chips obtained from conifers such as Japanese larch and Japanese cedar or broadleaf trees such as oil palm and Japanese cypress; pulps such as wood pulps obtained from wood and cotton linter pulps obtained from fibers around cotton seeds; stems, leaves and empty fruit bunches of plants such as bagasse (strained lees of sugarcane), rice straws, corn stems and leaves and palm empty fruit bunches (hereinafter referred to merely as "EFB"); shells of plants such as chaffs, palm shells and coconut shells; papers such as newspapers, corrugated boards, magazines and wood-free papers; and algae such as giant kelp, tangle, wakame, seaweed, gelidium amansii, spirulina, dunaliella, chlorella and scenedesmus. These lignocellulose raw materials may be used alone or in combination of any two or more thereof.

Of these lignocellulose raw materials, from the viewpoint of improving a yield of the lignin degradation product and a saccharification efficiency and from the viewpoints of a good availability and low costs for the raw materials, preferred are timbers, papers, stems, leaves and empty fruit bunches of plants, shells of plants and algae; more preferred are conifer chips, broadleaf tree chips, bagasse, rice straws, corn stems and leaves, EFB, chaffs, palm shells, coconut shells, papers and algae; still more preferred are bagasse, EFB and wood chips obtained from stems of oil palm; and further still more preferred is bagasse.

The content of lignin in the lignocellulose raw material is preferably not less than 5% by mass, more preferably not less than 10% by mass, and still more preferably not less than 15% by mass on the basis of the raw material, from the viewpoint of enhancing a yield of the lignin degradation product. The lignin content may be measured by the method described in Examples below.

(Pretreatment)

The lignocellulose raw material is preferably pretreated prior to subjecting the lignocellulose raw material to the enzymatic saccharification treatment from the viewpoints of enhancing a saccharification efficiency and a yield of the lignin degradation product and suppressing denaturation of lignin. The preferred pretreatment includes a milling treatment and a hydrothermal treatment. Of these pretreatments, from the viewpoint of suppressing denaturation of lignin, the milling treatment is preferred, whereas from the viewpoints of shortening the pretreatment time and enhancing a yield of the lignin degradation product, the hydrothermal treatment is preferred.

(Milling Treatment)

The lignocellulose raw material subjected to the milling treatment as the pretreatment can be formed into sufficiently small particles, so that a crystal structure of the cellulose contained in the lignocellulose raw material is broken to thereby improve a saccharification efficiency thereof.

In the case where the lignocellulose raw material is subjected to the milling treatment, the content of water in the lignocellulose raw material is preferably not more than 40% by mass, more preferably not more than 35% by mass, still more preferably not more than 30% by mass and further still more preferably not more than 20% by mass on the basis of the dry mass of the lignocellulose raw material from the viewpoint of improving a milling efficiency of the lignocellulose raw material and a yield of the lignin degradation product. Meanwhile, it is difficult to adjust the content of water in the lignocellulose raw material to 0% by mass. Therefore, the content of water in the lignocellulose raw material is preferably from 0.01 to 40% by mass, more preferably from 0.1 to 35% by mass, still more preferably from 1 to 30% by mass and further still more preferably from 1 to 20% by mass on the basis of the dry mass of the lignocellulose raw material.

The content of water in the lignocellulose raw material may be measured using a commercially available infrared aquameter or the like. More specifically, the content of water in the lignocellulose raw material may be measured by the method described in Examples below.

Meanwhile, in the case where the content of water in the lignocellulose raw material to be subjected to the milling treatment is more than 40% by mass, it is preferred that the lignocellulose raw material is dried by known methods (hereinafter also referred to as a "drying treatment") to adjust a content of water therein to not more than 40% by mass on the basis of the dry mass of the lignocellulose raw material. Examples of the drying method include a hot air heating drying method, a conduction heating drying method, a dehumidified air drying method, a chilled air drying method, a microwave drying method, an infrared drying method, a sun drying method, a vacuum drying method, a freeze drying method or the like. The drying device used in the drying treatment may be appropriately selected from conventionally known dryers. The drying treatment may be either a batch treatment or a continuous treatment.

The milling treatment may be carried out using conventionally known milling devices. The milling device used in the milling treatment is not particularly limited, and any milling device can be used as long as it is capable of forming the lignocellulose raw material into small particles and reducing a crystallinity of the cellulose.

Specific examples of the milling device include roll mills such as a high-pressure compression roll mill and a roll rotating mill; vertical roller mills such as a ring roller mill, a roller race mill and a ball race mill; tank-drive media mills such as a tumbling ball mill, a vibration ball mill, a vibration rod mill, a vibration tube mill, a planetary ball mill and a centrifugal fluid mill; media agitating mills such as a tower-type mill, an agitation tank mill, a flow tank mill and an annular mill; consolidated shear mills such as a high-speed centrifugal roller mill and an Angmill; and a mortar, a stone grist mill, a Masscolloider, a fret mill, an edge runner mil, a knife mill, a pin mill and cutter mill. Of these milling devices, from the viewpoints of a high milling efficiency of the lignocellulose raw material and a high productivity of the lignin degradation product, preferred are tank-drive media mills and media agitating mills, more preferred are tank-drive media mills, still more preferred are vibration mills such as a vibration ball mill, a vibration rod mill and a vibration tube mill, and further still more preferred is a vibration rod mill.

The milling treatment may be conducted in either batchwise or continuous manner. The material of the apparatus and/or media used in the milling treatment is not particularly limited, and selected from, for example, iron, stainless steel, alumina, zirconia, silicon carbide, silicon nitride and glass. Of these materials, preferred are iron, stainless steel, zirconia, silicon carbide and silicon nitride from the viewpoint of effectively breaking a crystal structure of the cellulose, and more preferred are iron and stainless steel from the viewpoint of industrial use.

If a vibration mill with rod media is used, the outer diameter of rods is preferably from 0.1 to 100 mm and more preferably from 0.5 to 50 mm from the viewpoint of a high milling efficiency of the lignocellulose raw material. If the size of rods is within the above range, the lignocellulose raw material can be effectively formed into sufficiently small particles, and the cellulose is free from contamination owing to inclusion of broken pieces of the rods.

The preferred filling rate of rod media may vary depending upon the type of vibration mill and is preferably from 10 to 97%, more preferably from 15 to 95% and still more preferably from 20 to 80%. When the filling rate of the rod media is within the above ranges, the frequency of contact between the lignocellulose raw material and the rod media is increased and the movement of media is not disturbed to increase the milling efficiency. The filling rate referred to herein is a ratio of the apparent volume of rod media to the volume of a stirring tank of the vibration mill.

The temperature used in the milling treatment is not particularly limited, and is preferably from −100 to 200° C., more preferably from 0 to 150° C. and still more preferably from 5 to 100° C. from the viewpoint of suppressing operating costs and deterioration in quality of the lignocellulose raw material.

The time of the milling treatment may be appropriately determined such that the lignocellulose raw material can be formed into sufficiently small particles after the milling treatment, and therefore may vary according to a milling device and an amount of energy used, etc. The time of the milling treatment is usually from 1 min to 12 h, and preferably from 2 min to 6 h, more preferably from 5 min to 3 h and still more preferably from 5 min to 2 h from the viewpoints of reducing a particle size of the lignocellulose raw material and saving energy costs.

Also, from the viewpoint of enhancing a milling efficiency of the lignocellulose raw material, a saccharification efficiency and a production efficiency (shortening a production time), the lignocellulose raw material is preferably subjected to the milling treatment in the presence of a basic compound.

(Basic Compound)

Examples of the basic compound used in the milling treatment include alkali metal hydroxides such as sodium hydroxide, potassium hydroxide and lithium hydroxide; alkaline earth metal hydroxides such as magnesium hydroxide and calcium hydroxide; alkali metal oxides such as sodium oxide and potassium oxide; alkaline earth metal oxides such as magnesium oxide and calcium oxide; alkali metal sulfides such as sodium sulfide and potassium sulfide; and alkaline earth metal sulfides such as magnesium sulfide and calcium sulfide. Of these basic compounds, from the viewpoint of enhancing an enzymatic saccharification rate, preferred are alkali metal hydroxides or alkaline earth metal hydroxides, more preferred are alkali metal hydroxides, and still more preferred is sodium hydroxide or potassium hydroxide. These basic compounds may be used alone or in combination of any two or more thereof.

The amount of the basic compound used in the milling treatment is preferably from 0.01 to 10 mol, more preferably from 0.05 to 8 mol, still more preferably from 0.1 to 5 mol and further still more preferably from 0.1 to 1.5 mol per 1 mol of an anhydroglucose unit constituting the cellulose (hereinafter also referred to merely as "AGU") assuming that all of holocelluloses in the lignocellulose raw material are celluloses. When the amount of the basic compound used is 0.01 mol or more per 1 mol of AGU, it is possible to enhance a saccharification efficiency in the below-mentioned step (2). Also, the amount of the basic compound used is preferably 10 mol or less per 1 mol of AGU from the viewpoints of good neutralization and/or facilitated cleaning ability of the basic compound as well as low costs of the basic compound.

When subjecting the lignocellulose raw material to milling treatment in the presence of the basic compound, the water content upon the milling treatment is preferably from 0.1 to 40% by mass, more preferably from 0.5 to 35% by mass, still more preferably from 1 to 30% by mass, further still more preferably from 1 to 25% by mass, and further still more preferably from 2 to 20% by mass on the basis of the dry mass of the lignocellulose raw material. When the water content upon the milling treatment lies within the above specified range, it is possible to enhance a milling efficiency of the lignocellulose raw material, and improve mixing, penetration and diffusion between the lignocellulose raw material and the basic compound, so that the saccharification treatment of the step (1) is allowed to proceed efficiently.

The water content upon the milling treatment as used herein means a content of water in the cellulose raw material based on the dry mass thereof, and may be appropriately controlled by reducing an amount of water contained in the cellulose raw material and the basic compound by drying these materials or by adding water upon the milling treatment to increase an amount of water present in the materials.

The average particle size of the lignocellulose raw material obtained after subjected to the milling treatment is preferably from 1 to 150 µm, and more preferably from 5 to 100 µm from the viewpoints of enhancing a yield of the lignin degradation product and a saccharification efficiency. Meanwhile, the average particle size of the lignocellulose raw material obtained after subjected to the milling treatment may be measured by the method described in Examples below.

The cellulose I-type crystallinity of the lignocellulose raw material obtained after subjected to the milling treatment is preferably from 0 to 40%, more preferably from 0 to 30%, still more preferably from 0 to 20% and further still more preferably from 0 to 10% from the viewpoints of enhancing a yield of the lignin degradation product and a saccharification efficiency. Meanwhile, the cellulose I-type crystallinity of the lignocellulose raw material obtained after subjected to the milling treatment may be measured by the method described in Examples below.

(Hydrothermal Treatment)

The hydrothermal treatment is such a treatment that a high-temperature aqueous solution acts on the lignocellulose raw material under pressurized conditions. The hydrothermal treatment may be conducted using a known reaction apparatus, and the reaction apparatus used in the hydrothermal treatment is not particularly limited. In the hydrothermal treatment, the lignocellulose raw material is preferably used in the form of a slurry. From the viewpoint of enhancing a saccharification efficiency, the hydrothermal treatment of the lignocellulose raw material is preferably conducted after subjecting the lignocellulose raw material to coarse pulverization. The content of the lignocellulose raw material in the slurry is preferably from 1 to 500 g/L, more preferably from 1 to 200 g/L, still more preferably from 5 to 150 g/L and further still more preferably from 8 to 100 g/L from the viewpoint of enhancing a fluidity of the slurry. The slurry may contain water, various buffer solutions, etc., as a medium thereof.

The hydrothermal treatment of the lignocellulose raw material is preferably carried out under an acid condition from the viewpoint of enhancing a production efficiency and a saccharification efficiency. The pH value of the slurry is preferably from 3 to 7 and more preferably from 4 to 6 from the viewpoints of enhancing a production efficiency and a saccharification efficiency, and suppressing denaturation of lignin. In addition, from the viewpoint of further enhancing a production efficiency and a saccharification efficiency, the pH value of the slurry is preferably from 1.5 to 3. The pH value of the slurry may be appropriately controlled by using an inorganic acid such as hydrochloric acid, sulfuric acid and phosphoric acid, or an organic acid such as acetic acid and citric acid.

The hydrothermal treatment is preferably conducted at a temperature of from 100 to 400° C.

The reaction temperature in the hydrothermal treatment is preferably not lower than 100° C., more preferably not lower than 120° C., still more preferably not lower than 130° C. and further still more preferably not lower than 140° C., and is also preferably not higher than 400° C., more preferably not higher than 300° C., still more preferably not higher than 220° C. and further still more preferably not higher than 200° C. from the viewpoint of enhancing a production efficiency and a saccharification efficiency of the cellulose. More specifically, the reaction temperature in the hydrothermal treatment is preferably from 100 to 400° C., more preferably from 120 to 300° C., still more preferably from 130 to 220° C., and further still more preferably from 140 to 200° C. from the viewpoint of enhancing a production efficiency and a saccharification efficiency of the cellulose.

The reaction pressure in the hydrothermal treatment is preferably not less than 0 MPa, more preferably not less than 0.01 MPa, still more preferably not less than 0.1 MPa and further still more preferably not less than 0.5 MPa, and is also preferably not more than 50 MPa, more preferably not more than 40 MPa and still more preferably not more than 20 MPa from the viewpoint of enhancing a production efficiency and a saccharification efficiency of the cellulose. More specifically, the reaction pressure in the hydrothermal treatment is preferably from 0 to 50 MPa, more preferably from 0.01 to 40 MPa, still more preferably from 0.1 to 20 MPa, and further still more preferably from 0.5 to 20 MPa from the viewpoint of enhancing a production efficiency and a saccharification efficiency of the cellulose.

The reaction time of the hydrothermal treatment is preferably not less than 0.0001 h, and is also preferably not more than 24 h, more preferably not more than 18 h and still more preferably not more than 12 h from the viewpoints of enhancing a production efficiency and a saccharification efficiency of the cellulose and suppressing denaturation of lignin. More specifically, the reaction time of the hydrothermal treatment is preferably from 0.0001 to 24 h, more preferably from 0.005 to 18 h, still more preferably from 0.01 to 12 h, further still more preferably from 0.02 to 6 h, further still more preferably from 0.02 to 3 h and further still more preferably from 0.02 to 1 h from the viewpoint of enhancing a production efficiency and a saccharification efficiency of the cellulose.

The hydrothermal treatment may be conducted in either batchwise or continuous manner.

Meanwhile, the lignocellulose raw material obtained by the hydrothermal treatment may be in a wet state or may be a dry product obtained by further subjecting the wet material to drying treatment. From the viewpoint of enhancing a saccharification efficiency, the lignocellulose raw material is preferably in a wet state.

(Saccharification Treatment)

As the enzyme used in the saccharification treatment of the step (1), there may be mentioned cellulase and hemcellulase from the viewpoints of improving a saccharification efficiency and a yield of a lignin degradation product and suppressing denaturation of lignin.

These enzymes may be used alone or in combination of any two or more thereof.

The cellulase means an enzyme capable of hydrolyzing a glycoside bond of β-1,4-glucane in cellulose, and is a generic name of enzymes called endoglucanase, exoglucanase or cellobiohydrolase, β-glucosidase and the like. As the cellulase used in the present invention, there may be mentioned commercially available cellulase preparations, and animal-, plant- and microorganism-derived cellulases.

Specific examples of the cellulase include cellulase preparations derived from *Trichoderma reesei*, such as "CELLUCLUST 1.5 L" (tradename) available from Novozymes and "CellicCTec2" (tradename) available from Novozymes; cellulases derived from strains of *Bacillus* sp. KSM-N145 (FERM P-19727); cellulases derived from respective strains of *Bacillus* sp. KSM-N252 (FERM P-17474), *Bacillus* sp. KSM-N115 (FERM P-19726), *Bacillus* sp. KSM-N440 (FERM P-19728), *Bacillus* sp. KSM-N659 (FERM P-19730) and the like; cellulase mixtures derived from *Trichoderma viride, Aspergillus acleatus, Clostridium thermocellum, Clostridium stercorarium, Clostridium josui Cellulomonas fimi, Acremonium celluloriticus, Irpex lacteus,*

*Aspergillus niger*, and *Humicola insolens*; and heat-resistant cellulases derived from *Pyrococcus horikoshii*.

Of these enzymes, from the viewpoint of improving a saccharification efficiency and a yield of the lignin degradation product, preferred are cellulases derived from *Trichoderma reesei, Trichoderma viride* or *Humicola insolens*, for example, "CELLUCLUST 1.5 L" (tradename) available from Novozymes, "TP-60" (tradename) available from Meiji Seika Pharma Co., Ltd., "CellicCTec2" (tradename) available from Novozymes, "Accellerase DUET" (tradename) available from Genencor, and "Ultraflo L" (tradename) available from Novozymes.

Specific examples of the β-glucosidase as one kind of cellulase include enzymes derived from *Aspergillus niger* (for example, such as "Novozyme 188" (tradename) available from Novozymes and β-glucosidase available from Megazyme), and enzymes derived from *Trichoderma reesei* and *Penicillium emersonii*.

Specific examples of the hemicellulase include hemicellulase preparations derived from *Trichoderma reesei* such as "CellicHTec2" (tradename) available from Novozymes, as well as xylanases derived from *Bacillus* sp. KSM-N546 (FERM P-19729), xylanases derived from *Aspergillus niger, Trichoderma viride, Humicola insolens* and *Bacillus alcalophilus*, and xylanases derived from *Thermomyce, Aureobasidium, Streptomyces, Clostridium, Thermotoga, Thermoascus, Caldocellum* and *Thermomonospora*.

The enzyme used in the step (1) is preferably at least one enzyme selected from the group consisting of the aforementioned cellulases and hemicellulases, more preferably at least one enzyme selected from the group consisting of cellobiohydrolase, β-glucosidase, endoglucanase and hemicellulase, and still more preferably at least one enzyme selected from the group consisting of cellobiohydrolase and endoglucanase.

The treating conditions used when subjecting the lignocellulose raw material to enzymatic saccharification treatment in the step (1) may be appropriately selected according to the content and cellulose I-type crystallinity of lignin in the lignocellulose raw material and the kind of enzyme used.

For example, in the case where the above-mentioned enzyme is used together with the lignocellulose raw material as a substrate, the above enzyme is added in an amount of from 0.001 to 15% (v/v) on the basis of a suspension containing the substrate in an amount of from 0.5 to 20% (w/v), and allowed to react therewith in a buffer solution having a pH value of from 2 to 10 at a temperature of from 10 to 90° C. for a reaction time of from 30 min to 5 days to subject the lignocellulose raw material to saccharification treatment.

The pH value of the buffer solution may be appropriately determined according to the kind of enzyme used, and is preferably from 3 to 7 and more preferably from 4 to 6.

The reaction temperature may also be appropriately determined according to the kind of enzyme used, and is preferably from 20 to 70° C. and more preferably from 40 to 60° C.

Further, the reaction time may also be appropriately determined according to the kind of enzyme used, and is preferably from 0.5 to 3 days and more preferably from 0.5 to 2 days.

(Saccharification Residue)

The lignocellulose raw material is subjected to saccharification treatment with the enzyme to obtain a saccharification residue. The term "saccharification residue" as used herein means a solid component separated from a mixture obtained after the enzymatic saccharification treatment by a solid-liquid separation method such as centrifugal separation. The solid component is washed with water several times to separate water-soluble polysaccharides therefrom. Thereafter, the saccharification residue may be subjected to the step (2) while kept in a wet state, or may be dried for powdering the residue. From the viewpoint of improving a production efficiency, it is preferred that the saccharification residue be subjected to the step (2) while kept in a wet state. Also, when subjected to the drying treatment, the saccharification residue is preferably dried at a temperature of 100° C. or lower, or more preferably freeze-dried, from the viewpoint of suppressing denaturation of lignin.

[Step (2)]

In the step (2), the above saccharification residue is subjected to heat treatment in a mixed solvent containing water and an organic solvent having a solubility in 20° C. water (hereinafter also referred to merely as a solubility) of not less than 90 g/L, thereby obtaining a heat treatment solution containing a lignin degradation product.

(Organic Solvent)

The organic solvent used together with water in the step (2) has a solubility in 20° C. water of not less than 90 g/L, preferably not less than 100 g/L, and still more preferably not less than 120 g/L from the viewpoints of readily separating lignin from cellulose and hemicellulose contained in the saccharification residue (hereinafter also referred to merely as a "lignin separability") and improving an extraction efficiency of the lignin degradation product. By using the organic solvent having a solubility in 20° C. water of not less than 90 g/L, it is possible to enhance an affinity between the mixed solvent and lignin and readily disentangle lignin from cellulose and hemicellulose so that an extraction efficiency of the lignin degradation product can be enhanced.

From the viewpoint of improving a lignin separability and an extraction efficiency of the lignin degradation product, the organic solvent is preferably at least one compound selected from the group consisting of alcohols, nitriles, ethers and ketones.

From the viewpoint of improving an extraction efficiency of the lignin degradation product, the organic solvent preferably has an SP value of from 8 to 23, more preferably from 8 to 16 and still more preferably from 9 to 13.

The term "SP value" as used herein means a solubility parameter. The solubility parameter is expressed by the value $\delta[(cal/cm^3)^{1/2}]$ determined based on the following Fedors' formula by a Fedors method [Robert F. Fedors, "Polymer Engineering and Science", 14, 147-154 (1974)] which value is calculated from a square root of a ratio of a sum (Dei) of evaporation energies of atoms or atomic groups in a chemical structure of a compound to a sum (Avi) of molar volumes thereof.

Fedors' formula: $\delta = (\Sigma \Delta ei / \Sigma \Delta vi)^{1/2}$

Specific examples of the organic solvent are as follows.

Specific examples of the alcohols include methanol, ethanol, diethylene glycol, n-propanol, isopropanol, 2-butanol, isobutanol and t-butyl alcohol.

Specific examples of the nitriles include acetonitrile and the like.

Specific examples of the ethers include dioxane and the like.

Specific examples of the ketones include acetone and methyl ethyl ketone.

The organic solvents illustrated above all have a solubility in 20° C. water of not less than 90 g/L. These organic solvents may be used alone or in combination of any two or more thereof.

Of these organic solvents, from the viewpoints of improving a lignin separability and an extraction efficiency of the lignin degradation product, and attaining a good safety, preferred is at least one compound selected from the group consisting of ethanol, isopropanol, acetonitrile, dioxane, acetone and methyl ethyl ketone; more preferred are ethanol, isopropanol and acetone; and still more preferred is acetone.

The ratio (molar ratio) of the organic solvent to water in the mixed solvent used in the step (2) [organic solvent/water] (mass ratio) is preferably from 90/10 to 10/90, more preferably from 70/30 to 30/70 and still more preferably from 60/40 to 40/60 from the viewpoint of improving a lignin separability and an extraction efficiency of the lignin degradation product.

In addition, the above mixed solvent preferably further contains an acid or a base from the viewpoints of enhancing a yield of the lignin degradation product and well controlling a molecular weight of the lignin degradation product.

Examples of the acid used in the mixed solvent include inorganic acids such as hydrochloric acid, sulfuric acid, nitric acid, phosphoric acid and boric acid; organic acids such as p-toluenesulfonic acid (PTSA), trifluoroacetic acid, trichloroacetic acid, formic acid, acetic acid and citric acid; Lewis acids such as aluminum chloride and metal triflates; fatty acids such as caprylic acid, pelargonic acid, capric acid, lauric acid, myristic acid, palmitic acid, stearic acid, oleic acid and linoleic acid; and heteropolyacids. Of these acids, from the viewpoints of enhancing a yield of the lignin degradation product and obtaining the low-molecular lignin degradation product, preferred is at least one acid selected from the group consisting of hydrochloric acid, sulfuric acid, PTSA and aluminum chloride.

Examples of the base used in the mixed solvent include alkali metal hydroxides such as sodium hydroxide, potassium hydroxide and lithium hydroxide; alkaline earth metal hydroxides such as magnesium hydroxide and calcium hydroxide; alkali metal oxides such as sodium oxide and potassium oxide; alkaline earth metal oxides such as magnesium oxide and calcium oxide; alkali metal sulfides such as sodium sulfide and potassium sulfide; and alkaline earth metal sulfides such as magnesium sulfide and calcium sulfide. Of these bases, from the viewpoints of enhancing a yield of the lignin degradation product and obtaining the high-molecular lignin degradation product, preferred is at least one base selected from the group consisting of alkali metal hydroxides and alkaline earth metal hydroxides, more preferred is at least one base selected from the group consisting of alkali metal hydroxides, and still more preferred is at least one base selected from the group consisting of sodium hydroxide and potassium hydroxide.

Meanwhile, the above acids or bases may be respectively used alone or in combination of any two or more thereof.

Also, the above mixed solvent preferably further contains a radical scavenger from the viewpoint of enhancing a yield of the lignin degradation product.

As the radical scavenger used in the mixed solvent, there may be mentioned aromatic radical scavengers, amine-based radical scavengers, stabilized free radical-based radical scavengers, organic acid-based radical scavengers, catechin-based radical scavengers and molecular hydrogen.

Examples of the aromatic radical scavengers include hydroquinone, benzoquinone, methoquinone (hydroquinone monomethyl ether), phenol, catechol, pyrogallol, 1,2,4-trihydroxybenzene, phlorogrucinol, resorcinol, homocatechol, p-cresol, 2-methoxyphenol, 2,4-dimethyl phenol, 2,6-dimethyl phenol, 2,6-dimethoxyphenol, 2-tert-butyl-4-methyl phenol, 2,6-di-tert-butyl-4-methyl phenol, 4-hydroxymethyl-2,6-di-tert-butyl phenol, 2,6-di-tert-butyl-4-ethyl phenol, butyl hydroxyanisole, n-octadecyl-3-(4-hydroxy-3,5-di-tert-butyl phenylpropionate, distearyl-(4-hydroxy-3-methyl-5-tert-butyl)benzyl malonate, propyl gallate, octyl gallate, dodecyl gallate, tocopherol, 2,2'-methylenebis(4-methyl-6-tert-butyl phenol), 2,2'-methylenebis(4-ethyl-6-tert-butyl phenol), 4,4'-methylenebis(2,6-di-tert-butyl phenol), 4,4'-butylidenebis(6-tert-butyl-m-cresol), 4,4'-thiobis(6-tert-butyl-m-cresol), styrenated phenol, N,N'-hexamethylenebis(3,5-di-tert-butyl-4-hydroxyhydrocinnamide), bis(3,5-di-tert-butyl-4-hydroxybenzyl phosphonic acid ethyl ester)calcium, 1,1,3-tris(2-methyl-4-hydroxy-5-tert-butyl phenyl)butane, 1,3,5-trimethyl-2,4,6-tris(3,5-di-tert-butyl-4-hydroxybenzyl)benzene, 1,6-hexanediol/bis[3-(3,5-di-tert-butyl-4-hydroxyphenyl)propionate], 2,2'-methylenebis(4-methyl-6-cyclohexyl phenol), 2,2'-methylenebis[6-(1-methylcyclohexyl-p-cresol], 1,3,5-tris(4-tert-butyl-3-hydroxy-2,6-dimethylbenzyl)isocyanuric acid, 1,3,5-tris(3,5-di-tert-butyl-4-hydroxybenzyl)isocyanuric acid, triethylene glycol/bis[3-(3-tert-butylo-4-hydroxy-5-methyl phenyl)propionate], 2,2'-oxaamide[ethyl/3-(3,5-di-tert-butyl-4-hydroxyphenyl)propionate], 6-(4-hydroxy-3,5-di-tert-butylanilino)-2,4-dioctylthio-1,3,5-triazine, bis[2-tert-butyl-4-methyl-6-(2-hydroxy-3-tert-butyl-5-methylbenzyl) phenyl]terephthalate, 3,9-bis[2-[3-(3-tert-butyl-4-hydroxy-5-methyl phenyl)propionyloxy]-1,1-dimethylethyl]-2,4,8,10-tetraoxaspiro[5.5]undecane and 3,9-bis[2-[3-(3,5-di-tert-butyl-4-hydroxyphenynpropionyloxy]-1,1-dimethylethyl]-2,4,8,10-tetraoxaspiro[5.5]undecane.

Examples of the amine-based radical scavenger include tributylamine, diphenylamine, phenothiazine and phenyl-α-naphthyl amine.

Examples of the stabilized free radical-based radical scavenger include 2,2,6,6-tetramethyl piperidine-1-oxyl and the like.

Examples of the organic acid-based radical scavenger include L-ascorbic acid, erythorbic acid, α-tocopherol and chlorogenic acid.

Examples of the catechin-based radical scavenger include (+)-catechin, epicatechin, epigallocatechin, epigallocatechin gallate and epigallocatechin gallate.

Of these radical scavengers, from the viewpoint of enhancing a yield of the lignin degradation product, preferred is at least one radical scavenger selected from the group consisting of aromatic radical scavengers, amine-based radical scavengers, organic acid-based radical scavengers, catechin-based radical scavengers and molecular hydrogen, more preferred is at least one radical scavenger selected from the group consisting of aromatic radical scavengers and organic acid-based radical scavengers, and still more preferred are aromatic radical scavengers.

More specifically, as the aromatic radical scavengers, preferred is at least one radical scavenger selected from the group consisting of hydroquinone, benzoquinone, methoquinone (hydroquinone monomethyl ether), phenol, catechol, pyrogallol, 1,2,4-trihydroxybenzene, phlorogrucinol, resorcinol, homocatechol, p-cresol, 2-methoxyphenol, 2,4-dimethyl phenol, 2,6-dimethyl phenol, 2,6-dimethoxyphenol, 2,6-di-tert-butyl-4-methyl phenol and butylhydroxyanisole, more preferred is at least one radical scavenger selected from the group consisting of hydroquinone, benzoquinone, methoquinone (hydroquinone monomethyl ether), phenol, catechol, pyrogallol, 1,2,4-trihydroxybenzene, phlorogrucinol, p-cresol, 2-methoxyphenol and 2,6-di-tert-butyl-4-methyl phenol, and still more preferred is at least one radical scavenger selected from the group consisting of hydroquinone, benzoquinone, methoquinone (hydroquinone monomethyl ether) and phenol.

The amount of the mixed solvent used in the step (2) is from 2 to 40 times, more preferably from 2 to 30 times, still more preferably from 3 to 30 times and further still more preferably from 5 to 30 times the mass of a solid component of the saccharification residue from the viewpoint of enhancing a productivity and a degradability of lignin.

The content of the acid or base in the mixed solvent used in the step (2) is preferably from 0.001 to 1.0% by mass and more preferably from 0.01 to 0.5% by mass on the basis of the mixed solvent from the viewpoints of enhancing a yield of the lignin degradation product and well controlling a molecular weight of the lignin degradation product produced.

The content of the radical scavenger in the mixed solvent is preferably from 5 to 1000 mol %, more preferably from 6 to 500 mol %, still more preferably from 8 to 200 mol % and further still more preferably from 10 to 100 mol % on the basis of the number of moles of the lignin in the saccharification residue used in the step (2). The number of moles of lignin in the saccharification residue is the value obtained by dividing the content of lignin in the saccharification residue by 180.22 as a molecular weight of coniferyl alcohol assuming that a constitutional monomer of lignin is the coniferyl alcohol.

The temperature of the heat treatment in the step (2) is preferably from 40 to 300° C., more preferably from 80 to 280° C., still more preferably from 100 to 250° C. and further still more preferably from 120 to 200° C. from the viewpoints of suppressing denaturation of lignin and enhancing a yield of the lignin degradation product.

The heating device used in the step (2) is preferably an autoclave or a microwave heater from the viewpoints of suppressing denaturation of lignin and enhancing a yield of the lignin degradation product.

The reaction pressure upon the heat treatment in the step (2) is preferably from 0.1 to 30 MPa, more preferably from 0.1 to 20 MPa and still more preferably from 0.1 to 15 MPa from the viewpoints of suppressing denaturation of lignin and enhancing a yield of the lignin degradation product.

The time of the heat treatment in the step (2) is not particularly limited and may be appropriately determined according to the amount of the saccharification residue produced, and is preferably from 1 min to 5 h, more preferably from 1 min to 3 h and still more preferably from 2 min to 2 h from the viewpoints of suppressing denaturation of lignin and enhancing a yield of the lignin degradation product.

(Step (3))

In the step (3), the heat treatment solution containing the lignin degradation product obtained in the step (2) is subjected to solid-liquid separation to remove insoluble components therefrom, thereby obtaining the lignin degradation product.

The method of obtaining the lignin degradation product is not particularly limited as long as the method includes at least a step of subjecting the heat treatment solution obtained in the step (2) to solid-liquid separation to remove insoluble components therefrom and obtain the lignin degradation product contained in a liquid component thus separated. As the method of obtaining the lignin degradation product, there may be mentioned solid-liquid separation such as filtration and centrifugal separation which may be appropriately used in combination with various steps such as removal of solvents by distillation, washing and drying.

Also, if the acid or base is added in the above step (2), the step (3) may also include a neutralization step. These steps may be conducted by ordinary methods. For example, there may be used such a method in which the heat treatment solution obtained in the step (2) is subjected to solid-liquid separation to remove insoluble components therefrom, and after removing the organic solvent and water contained in the liquid component by distillation under reduced pressure, the resulting residue was washed with water to obtain the lignin degradation product. By washing the residue obtained after removal of the solvent by distillation with water, it is possible to remove water-soluble polysaccharides or the like, so that the purity of lignin in the lignin degradation product can be enhanced.

[Lignin Degradation Product]

The lignin degradation product obtained by the production process of the present invention has a low degree of denaturation and a good solubility in solvents, and therefore can be effectively used as a material capable of being converted into low-molecular aromatic compounds such as vanillin, syringaldehyde, p-hydroxybenzaldehyde, vanillic acid, syringic acid and 4-hydroxybenzoic acid. Also, the lignin degradation product may be used directly as an antibacterial agent, an agricultural chemical, and a thermosetting resin, a cement dispersant, a dispersant for secondary batteries, additives for perfumes and cosmetics, and other functional materials.

The weight-average molecular weight of the lignin degradation product obtained by the production process of the present invention is, for example, in the range of from 2,000 to 40,000, and may be appropriately selected according to the applications of the lignin degradation product.

The aldehyde yield rate as an index of a degree of denaturation of the lignin degradation product obtained by the production process of the present invention is preferably not less than 10%, more preferably not less than 12.5%, still more preferably not less than 15% and further still more preferably not less than 20% from the viewpoint of conversion into low-molecular aromatic compounds. Meanwhile, the aldehyde yield rate is the value measured by an alkaline nitrobenzene oxidation method described in Examples below. The higher the aldehyde yield rate becomes, the lower the degree of denaturation of the lignin degradation product is.

With respect to the above embodiments of the present invention, there are described the following aspects concerning the process for producing the lignin degradation product, and the lignin degradation product.

[1] A process for producing a lignin degradation product, including the following steps (1) to (3):

Step (1): subjecting a lignocellulose raw material to enzymatic saccharification treatment to obtain a saccharification residue;

Step (2): subjecting the saccharification residue obtained in the step (1) to heat treatment in a mixed solvent containing water and an organic solvent having a solubility in 20° C. water of not less than 90 g/L, preferably not less than 100 g/L and more preferably not less than 120 g/L to obtain a heat treatment solution containing the lignin degradation product; and Step (3): subjecting the heat treatment solution obtained in the step (2) to solid-liquid separation to remove insoluble components from the heat treatment solution, thereby obtaining the lignin degradation product.

[2] The process for producing a lignin degradation product as described in the above aspect [1], wherein a ratio of the organic solvent to water [organic solvent/water] (mass ratio)

in the mixed solvent is from 90/10 to 10/90, preferably from 70/30 to 30/70 and more preferably from 60/40 to 40/60.

[3] The process for producing a lignin degradation product as described in the above aspect [1] or [2], wherein an SP value of the organic solvent is from 8 to 23, preferably from 8 to 16 and more preferably from 9 to 13.

[4] The process for producing a lignin degradation product as described in any one of the above aspects [1] to [3], wherein the organic solvent is at least one compound selected from the group consisting of alcohols, nitriles, ethers and ketones.

[5] The process for producing a lignin degradation product as described in any one of the above aspects [1] to [4], wherein the organic solvent is at least one compound selected from the group consisting of ethanol, isopropanol, acetonitrile, dioxane, acetone and methyl ethyl ketone, preferably at least one compound selected from the group consisting of ethanol, isopropanol and acetone, and more preferably acetone.

[6] The process for producing a lignin degradation product as described in any one of the above aspects [1] to [5], wherein the mixed solvent further comprises an acid or a base.

[7] The process for producing a lignin degradation product as described in the above aspect [6], wherein a content of the acid or base in the mixed solvent used in the step (2) is from 0.001 to 1.0% by mass and preferably from 0.01 to 0.5% by mass on the basis of the mixed solvent.

[8] The process for producing a lignin degradation product as described in any one of the above aspects [1] to [7], wherein the mixed solvent further comprises a radical scavenger, preferably at least one radical scavenger selected from the group consisting of an aromatic radical scavenger, an amine-based radical scavenger, a stabilized free radical-based radical scavenger, an organic acid-based radical scavenger, a catechin-based radical scavenger and a molecular hydrogen, more preferably at least one radical scavenger selected from the group consisting of an aromatic radical scavenger, an amine-based radical scavenger, an organic acid-based radical scavenger, a catechin-based radical scavenger and a molecular hydrogen, still more preferably at least one radical scavenger selected from the group consisting of an aromatic radical scavenger and an organic acid-based radical scavenger, and further still more preferably an aromatic radical scavenger.

[9] The process for producing a lignin degradation product as described in the above aspect [8], wherein a content of the radical scavenger in the mixed solvent is from 5 to 1000 mol %, preferably from 6 to 500 mol %, more preferably from 8 to 200 mol %, and still more preferably from 10 to 100 mol % on the basis of number of moles of lignin in the saccharification residue.

[10] The process for producing a lignin degradation product as described in any one of the above aspects [1] to [9], wherein the mixed solvent is used in an amount being from 2 to 40 times, preferably from 2 to 30 times, more preferably from 3 to 30 times, and still more preferably from 5 to 30 times a mass of a solid component in the saccharification residue.

[11] The process for producing a lignin degradation product as described in any one of the above aspects [1] to [10], wherein a temperature of the heat treatment in the step (2) is from 40 to 300° C., preferably from 80 to 280° C., more preferably from 100 to 250° C., and still more preferably from 120 to 200° C.

[12] The process for producing a lignin degradation product as described in any one of the above aspects [1] to [11], wherein the lignocellulose raw material is subjected to a milling treatment or a hydrothermal treatment prior to the enzymatic saccharification treatment.

[13] The process for producing a lignin degradation product as described in any one of the above aspects [1] to [11], wherein the lignocellulose raw material is subjected to a milling treatment prior to the enzymatic saccharification treatment.

[14] The process for producing a lignin degradation product as described in the above aspect [12] or [13], wherein in the milling treatment, a content of water in the lignocellulose raw material is not more than 40% by mass, preferably from 0.01 to 40% by mass, more preferably from 0.1 to 35% by mass, still more preferably from 1 to 30% by mass, and further still more preferably from 1 to 20% by mass on the basis of a dry mass of the lignocellulose raw material.

[15] The process for producing a lignin degradation product as described in any one of the above aspects [12] to [14], wherein a time of the milling treatment is from 1 min to 12 h, preferably from 2 min to 6 h, more preferably from 5 min to 3 h, and still more preferably from 5 min to 2 h.

[16] The process for producing a lignin degradation product as described in any one of the above aspects [12] to [15], wherein the milling treatment is carried out in the presence of a basic compound.

[17] The process for producing a lignin degradation product as described in the above aspect [16], wherein a content of water upon the milling treatment is from 0.1 to 40% by mass, preferably from 0.5 to 35% by mass, more preferably from 1 to 30% by mass, still more preferably from 1 to 25% by mass, and further still more preferably from 2 to 20% by mass on the basis of a dry mass of the lignocellulose raw material.

[18] The process for producing a lignin degradation product as described in the above aspect [16] or [17], wherein an amount of the base compound used upon the milling treatment is from 0.01 to 10 mol, preferably from 0.05 to 8 mol, more preferably from 0.1 to 5 mol, and still more preferably from 0.1 to 1.5 mol per 1 mol of an anhydroglucose unit constituting the cellulose.

[19] The process for producing a lignin degradation product as described in any one of the above aspects [1] to [11], wherein the lignocellulose raw material is subjected to a hydrothermal treatment prior to the enzymatic saccharification treatment.

[20] The process for producing a lignin degradation product as described in the above aspect [12] or [19], wherein a reaction temperature used in the hydrothermal treatment is from 100 to 400° C., preferably from 120 to 300° C., more preferably from 130 to 220° C., and still more preferably from 140 to 200° C.

[21] The process for producing a lignin degradation product as described in any one of the above aspects [12], [19] and [20], wherein a reaction pressure used in the hydrothermal treatment is from 0 to 50 MPa, preferably from 0.01 to 40 MPa, more preferably from 0.1 to 20 MPa, and still more preferably from 0.5 to 20 MPa.

[22] The process for producing a lignin degradation product as described in any one of the above aspects [12] and [19] to [21], wherein a reaction time in the hydrothermal treatment is from 0.0001 to 24 h, preferably from 0.0001 to 18 h, and more preferably from 0.0001 to 12 h.

[23] The process for producing a lignin degradation product as described in any one of the above aspects [1] to [22], wherein the enzyme is at least one enzyme selected from the group consisting of cellulases and hemicellulases, preferably at least one enzyme selected from the group consisting of cellobiohydrolase, β-glucosidase, endoglucanase and hemicellulases, and more preferably at least one enzyme selected from the group consisting of cellobiohydrolase and endoglucanase.

[24] The process for producing a lignin degradation product as described in any one of the above aspects [1] to [23], wherein the lignocellulose raw material is at least one material selected from the group consisting of conifer chips, broadleaf tree chips, bagasse, rice straws, corn stems and leaves, palm empty fruit bunches (EFB), chaffs, palm shells, coconut shells, papers and algae, preferably bagasse, EFB or wood chips obtained from oil palm, and more preferably bagasse.

[25] A lignin degradation product produced by the process as described in any one of the above aspects [1] to [24].

[26] The lignin degradation product as described in the above aspect [25], wherein the lignin degradation product has an aldehyde yield rate of not less than 10%, preferably not less than 12.5%, more preferably not less than 15%, and still more preferably not less than 20% as measured by an alkaline nitrobenzene oxidation method.

EXAMPLES

In the following Examples and Comparative Examples, the term "%" indicates "% by mass", unless otherwise noted. The methods of measuring and evaluating various properties are as follow.

(1) Calculation of Content of Holocellulose in Lignocellulose Raw Material

The lignocellulose raw material was milled, and subjected to Soxhlet extraction with a mixed solvent containing ethanol and dichloroethane (at a mass ratio of 1:1) for 6 h. The obtained extracted sample was dried under vacuum at 60° C. Added to 2.5 g of the thus obtained sample were 150 mL of water, 1.0 g of sodium chlorite and 0.2 mL of acetic acid, and the resulting mixture was heated at a temperature of from 70 to 80° C. for 1 h. Successively, the procedure including the steps of adding the sodium chlorite and acetic acid and heating the resulting mixture was repeated 3 or 4 times until the sample was decolored whitely. The thus obtained white residue was filtered through a glass filter (1G-3) and washed with chilled water and acetone, and then dried to constant weight at 105° C. to determine a mass of the residue. From the following formula, the content of holocellulose in the lignocellulose raw material was calculated and defined as a cellulose content therein.

Cellulose content(mass %)=[mass of residue(g)/mass of lignocellulose raw material sampled(g; in terms of mass of dried raw material)]×100

(2) Calculation of Number of Moles of Anhydroglucose Units (AGU)

The number of moles of AGU was calculated from the following formula assuming that all of holocelluloses in the lignocellulose raw material are celluloses.

Number of moles of AGU=mass of holocelluloses (g)/162

(3) Measurement of Content of Water in Lignocellulose Raw Material

The content of water in the lignocellulose raw material was measured by using an infrared moisture tester (tradename "FD-610" manufactured by Kett Electric Laboratory). The measurement was conducted at 150° C., and the point where the mass change with time for 30 s was 0.1% or less was taken as the end point of the measurement. The thus measured water content was converted into percent(s) by mass based on a dry mass of the lignocellulose raw material.

(4) Method of Measuring Crystallinity of Milled Product of Lignocellulose Raw Material Each sample was measured for an intensity of X-ray diffraction under the following conditions by using "Rigaku RINT 2500VC X-RAY Diffractometer" manufactured by Rigaku Corporation, and the crystallinity of the sample was calculated from the following calculation formula (I).

Measuring Conditions

X-ray source: Cu/$K_\alpha$-radiation,
Tube voltage: 40 kV,
Tube current: 120 mA,
Measuring range: 2θ=5 to 45°, and A compressed pellet having a surface area of 320 $mm^2$ and a thickness of 1 mm was prepared and used as the sample for measurement. The measurement was conducted at an X-ray scan speed of 10°/min.

[Cellulose I-Type Crystallinity]

The cellulose I-type crystallinity was calculated by Segal method from a diffraction intensity value obtained by an X-ray diffraction method, and defined by the following calculation formula (1):

$$\text{Cellulose } I\text{-Type Crystallinity}(\%)=[(I_{22.6}-I_{18.5})/I_{22.6}]\times 100 \quad (1)$$

wherein $I_{22.6}$ is a diffraction intensity of a lattice plane (002 plane) as measured at a diffraction angle 2θ of 22.6° in X-ray diffraction analysis; and $I_{18.5}$ is a diffraction intensity of an amorphous moiety as measured at a diffraction angle 2θ of 18.5° in X-ray diffraction analysis.

(5) Method of Measuring Average Particle Size of Milled Product of Lignocellulose Raw Material The average particle size was measured using a laser diffraction/scattering particle size distribution analyzer (tradename "LA-950" manufactured by Horiba Ltd.). More specifically, prior to the measurement, a sample to be measured was subjected to ultrasonic treatment for 1 min to disperse the sample in water as a dispersing medium, and a median diameter of the sample on the basis of a volume thereof was measured at room temperature.

(6) Calculation of Content of Lignin in Lignocellulose Raw Material

The content of lignin in the lignocellulose raw material was calculated from the following formula. Meanwhile, the content of lignin in each of the enzymatic saccharification residue as an initial substrate in the step (2) and the final reside obtained in the step (2) was determined by the same method.

Lignin Content(g)=[true acid-insoluble lignin content (%)+acid-soluble lignin content(%)]×mass of sample(on a dry basis)(g)/100

In the above formula, the true acid-insoluble lignin content and the acid-soluble lignin content are calculated by the following methods.

(Calculation of True Acid-Insoluble Lignin Content)

The true acid-insoluble lignin content was calculated by subtracting an ash content from a crude acid-insoluble lignin content according to the following formula.

True Acid-Insoluble Lignin Content(%)=crude acid-insoluble lignin content(%)×[100−ash content (%)]/100

(Calculation of Crude Acid-Insoluble Lignin Content)

The milled lignocellulose raw material was dried under vacuum at 60° C. The thus dried sample in an amount of 300 mg was placed in a vial, and 3 mL of 72% sulfuric acid was added thereto, and the resulting mixture was adequately stirred in a water bath at 30° C. for 1 h. Thereafter, the mixture was mixed with 84 mL of water and transferred into a pressure bottle, and then treated in an autoclave at 120° C. for 1 h. Then, the sample was taken out from the autoclave before its temperature was dropped to 70° C. or lower, and subjected to suction filtration using a 1G-3 glass filter whose constant weight was previously measured. The resulting filtrate (A) was stored, whereas the glass filter attached with a residue was fully washed with water and then dried at 105° C. to measure a constant weight thereof, thereby determining a mass of the crude acid-insoluble lignin sampled (on a dry basis) according to the following formula.

Crude Acid-Insoluble Lignin Content(%)=[mass of lignin residue(g)/mass of sample(on a dry basis) (g)]×100

(Calculation of Ash Content)

The crude acid-insoluble lignin was transferred into a crucible whose constant weight was previously measured, held therein at 575° C. for 12 h, and then cooled to measure a constant weight of the crucible and determine a mass of the sample after ashing. The ash content was calculated from the following formula.

Ash Content(%)=[mass of sample after ashing(g)/ mass of crude acid-insoluble lignin sampled(on a dry basis)(g)]×100

(Calculation of Acid-Soluble Lignin Content)

The acid-soluble lignin content was measured by the following method.

The filtrate (A) was sampled in a constant volume of 100 mL and measured for an absorbance thereof at 205 nm using an absorptiometer "UV-Vis". In this case, the filtrate was adequately diluted such that the absorbance thereof was in the range of from 0.3 to 0.8.

Acid-Soluble Lignin Content(%)=$d×v×(As-Ab)/(a×w)×100$ wherein d: dilution ratio; v: constant volume (L) of filtrate; As: absorbance of sample solution; Ab: absorbance of blank solution; a: absorptivity coefficient of lignin; w: mass of sample (on a dry basis) (g).

As the absorptivity coefficient (a) of lignin, there was used 110 L/g/cm as the value described as the known average value in a reference document ("Methods in Lignin Chemistry", UNI Publishing Co., Ltd.).

(7) Method of Measuring Rate of Extraction of Lignin

The lignin extraction rate was calculated as follows.

(In the Case of Enzymatic Saccharification Residue)

Lignin Extraction Rate(mass %)=[(mass of enzymatic saccharification residue charged(g)×lignin content in enzymatic saccharification residue (%))–(mass of final residue obtained in step(2) (g)×lignin content in final residue obtained in step(2)(%))]/[mass of enzymatic saccharification residue charged(g)×lignin content in enzymatic saccharification residue(%)]×100×K K=[mass of enzymatic saccharification residue recovered(g)×lignin content in enzymatic saccharification residue(%)]/[mass of lignocellulose raw material charged(g)×lignin content in lignocellulose raw material(%)]

Meanwhile, the final residue obtained in the step (2) means an insoluble component contained in the heat treatment solution obtained in the step (2).

(In the Case of Kraft Cooking Method)

Lignin Extraction Rate(mass %)=[mass of Kraft-cooked lignin recovered(g)×lignin content in Kraft-cooked lignin(%)]/[mass of lignocellulose raw material charged(g)×lignin content in lignocellulose raw material(%)]

(8) Method of Measuring Weight-Average Molecular Weight of Lignin

The molecular weight of lignin produced according to the process of the present invention was measured by gel chromatographic method under the following conditions.

Two columns "TSK-GEL α-M" available from Tosoh Corp, and a guard column were connected to the GPC apparatus "HLC-8120GPC" available from Tosoh Corp. N,N-dimethyl formamide in which $H_3PO_4$ and LiBr were dissolved in amounts of 60 mmol/L and 50 mmol/L, respectively, as an eluent, was allowed to flow through the columns at a flow rate of 1 mL/min, and the columns were stabilized in a thermostat at 40° C. One hundred microliters of the sample solution was injected to the columns to measure a molecular weight of the sample. The molecular weight of the sample was calculated on the basis of a calibration curve previously prepared. The calibration curve of the molecular weight was prepared by using several kinds of monodisperse polystyrenes ("A-500" (molecular weight: $5.0×10^2$), "F-10" (molecular weight: $9.64×10^4$) and "F-850" (molecular weight: $8.42×10^6$) all available from Tosoh Corporation; and those monodisperse polystyrenes having molecular weights of $4.0×10^3$, $3.0×10^4$ and $9.29×10^5$ available from Pressure Chemical) as reference standard samples.

(9) Method of Measuring Degree of Denaturation of Lignin

The degree of denaturation of lignin was evaluated from an aldehyde yield rate thereof as an index using an alkaline nitrobenzene oxidation method described in a reference document ("Methods in Lignin Chemistry", UNI Publishing Co., Ltd.). More specifically, the degree of denaturation of lignin was measured by the following method.

That is, about 200 mg of the lignocellulose raw material (40 to 60 mesh) or 50 mg of purified lignin as a sample was weighed. The sample, 7 mL of a 2M sodium hydroxide aqueous solution and 0.4 mL of nitrobenzene were charged into a 20 mL vial and heated at 170° C. for 2.5 h while stirring at 900 rpm. After completion of the reaction, the resulting reaction solution was cooled and then extracted with 10 mL of diethyl ether three times to remove a reduced product of nitrobenzene and an excess amount of nitrobenzene therefrom. Concentrated hydrochloric acid was added to the remaining water layer to adjust a pH value thereof to 1, and the obtained solution was extracted with 10 mL of diethyl ether three times. The resulting diethyl ether extraction solution was subjected to distillation under reduced pressure to obtain an oxidation mixture. The resulting mixture was diluted with 20 mL of dichloromethane in a measuring cylinder. Then, 2 mL of the obtained dilute solution was filtered through a Millipore HVHP membrane (available from Millipore Japan; pore size: 0.45 μm) and subjected to gas chromatography (GC).

The conditions for the gas chromatography were as follows. That is, a GC apparatus (available from Agilent Technologies Inc.) equipped with a column "Agilent J & W GC Column DB-5" (available from Agilent Technologies Inc.) was used under the following conditions: amount of sample: 1.0 μL; helium flow rate; 10 mL/min; injection port temperature: 200° C.; split ratio: 10:1. The temperature condition was adjusted such that the reaction system was held at a temperature of 60° C. for 1 min, raised up to the range of from 60 to 250° C. at a rate of 5° C./min, and held at 250° C. for 10 min. The quantitative determination of the sample was conducted using a calibration curve prepared with respect to a peak area based on a concentration of respective reagents including vanillin, syringaldehyde and p-hydroxybenzaldehyde to thereby determine an amount of each aldehyde produced in the sample.

A sum of amounts of the three aldehydes produced was defined as an aldehyde yield in the sample. The aldehyde yield rate (%) as an index of the degree of denaturation of lignin was calculated by dividing the aldehyde yield by a mass of lignin in the sample charged.

As the aldehyde yield rate increases, the lignin degradation product having a lower degree of denaturation can be produced.

(10) Evaluation of Solubility in Solvents of Lignin Degradation Product

Sampled into a vial was 1 mg of the resulting lignin degradation product, and 1 mg of a solvent was added thereto. The resulting solution was stirred to visually evaluate a solubility of lignin in the solvent. As the solvent, there was used dimethyl sulfoxide (DMSO) or dimethyl formamide (DMF).

Example 1

Pretreatment

Bagasse (strained lees of sugarcane; water content: 7.0%) as a lignocellulose raw material was placed in a vacuum dryer ("VO-320" (tradename) available from Advantec Toyo Kaisha, Ltd.), and dried under reduced pressure in a nitrogen flow for 2 h, thereby obtaining dried bagasse having a water content of 2.0%, a holocellulose content of 71.3% by mass and a lignin content of 22.8%.

The thus obtained dried bagasse was weighed in an amount of 100 g and charged into a batch-type vibration mill ("MB-1" (tradename) available from Chuo Kakohki Co., Ltd.; total container capacity: 3.5 L; filled with SUS304 rods with a circular shape in section having a diameter of ϕ30 mm and a length of 218 mm, at a filling ratio of 57%), and subjected to milling treatment for 10 min, thereby obtaining a milled bagasse (cellulose I-type crystallinity: 0%; average particle size: 68.0 μm).

[Step (1)]

The thus obtained milled bagasse was weighed in an amount of 100 g and charged into 2.0 L of a 100 mM acetic acid buffer solution (pH: 5.0), and 20 mL of a cellulose/hemicellulase preparation ("Cellic CTec 2") available from Novozymes was added thereto. The resulting mixture was held at 50° C. while stirring at 600 rpm to subject the mixture to enzymatic saccharification. After 24 h, the reaction was terminated, and the resulting reaction solution was subjected to centrifugal separation to separate the solution into a supernatant solution and a saccharification residue. The saccharification residue was subjected to repeated washing and centrifugal separation steps and then to freeze-drying. The content of lignin in the saccharification residue was measured by the above method.

[Step (2)]

The saccharification residue (absolute dry mass: 250 mg) was charged into a reaction vessel (capacity: 5 mL), and 4.8 g of a mixed solvent of acetone/water (mass ratio: 50/50) was added thereto. Then, the reaction vessel was hermetically closed, and the contents of the reaction vessel were subjected to microwave heating at 160° C. under 1.6 MPa for 30 min while stirring at 900 rpm using a microwave heater "Initiator 60" (available from Biotage Japan Ltd.), thereby obtaining a heat treatment solution.

[Step (3)]

The heat treatment solution obtained in the step (2) was subjected to centrifugal separation to separate the solution into an extraction solution and a residue. The resulting residue was washed with acetone, water and a mixed solvent of acetone and water until an extraction solution therefrom became transparent. The extraction solutions from the centrifugal separation and washing were collected and subjected to distillation under reduced pressure to remove the solvents contained in the extraction solution. The resulting solids were washed again with water, and the obtained water-insoluble components were dried under reduced pressure at room temperature, thereby obtaining 94 mg of a lignin degradation product. The results are shown in Tables 1 and 2.

Example 2

The same procedure as in Example 1 was repeated except that 240 μL of hydrochloric acid (concentration: 1.0 M) was added to the solvent in the step (2), and 240 μL of 1.0 M sodium hydroxide was added to the extraction solutions collected in the step (3) to neutralize the extraction solutions. The results are shown in Tables 1 and 2.

Example 3

The same procedure as in Example 2 was repeated except that the following pretreatment was conducted, and the resulting milled bagasse was subjected to the step (1). The results are shown in Tables 1 and 2.

(Pretreatment)

One hundred grams of the dried bagasse obtained in the same manner as in Example 1, and 4.4 g (corresponding to 0.25 mol per 1 mol of AGU constituting the holocellulose) of granular sodium hydroxide having a particle size of 0.7 mm ("TOSOH PEARL" (tradename) available from Tosoh Corp.) were charged into a batch-type vibration mill, and subjected to milling treatment for 2 h, thereby obtaining a milled bagasse (cellulose I-type crystallinity: 14%; average particle size: 56.6 μm). One hundred grams of the thus obtained milled bagasse (in terms of the dry raw material except for the base compound) was neutralized with 1.0 M hydrochloric acid.

Comparative Example 1

The bagasse as the raw material was mixed with NaOH/$Na_2S$/$Na_2CO_3$ (=103.7/41.4/32.7 in terms of $Na_2O$, mass ratio; active alkali addition rate: 16.5% based on absolute dry bagasse in terms of $Na_2O$) and 0.05% of anthraquinone such that a solid-liquid ratio of the resulting mixture was 5 L/kg-bagasse. The mixture was heated at 170° C. for 90 min while stirring. After completion of the reaction, the obtained reaction mixture was subjected to solid-liquid separation, and the resulting filtrate was neutralized with hydrochloric acid to precipitate a solid fraction therefrom. The thus precipitated fraction was separated by solid-liquid separation, thereby obtaining Kraft-cooked lignin. The results are shown in Table 1.

Comparative Example 2

One hundred grams of the dried bagasse obtained in the same manner as in Example 1 was charged into a batch-type vibration mill ("MB-1" (tradename) available from Chuo Kakohki Co., Ltd.; total container capacity: 3.5 L; filled with SUS304 rods with a circular shape in section having a diameter of ϕ30 mm and a length of 218 mm, at a filling ratio of 57%), and subjected to milling treatment for 2 h, thereby obtaining a milled bagasse (crystallinity: 0%; average particle size: 55.4 μm). Next, the subsequent procedure was conducted in the same manner as in Example 1 except that the step (1) was omitted, and the milled bagasse was used as the raw material in the strep (2). The results are shown in Table 1.

Comparative Example 3

The same procedure as in Example 1 was repeated except that the contents of the reaction vessel were stirred at a normal temperature (25° C.) under normal pressures for 30 min. The results are shown in Table 1.

Example 8

The same procedure as in Example 5 was repeated except that ethanol was used in place of acetone in the step (2), and the reaction pressure was left without any control. The results are shown in Table 2.

Examples 9 to 12

The same procedure as in Example 1 was repeated except that acetonitrile (Example 9), methyl ethyl ketone (Example 10), dioxane (Example 11) and isopropanol (Example 12) were respectively used in place of acetone in the step (2), and the reaction pressure was left without any control. The results are shown in Table 2.

TABLE 1

|  | Examples | | | Comparative Examples | | |
| --- | --- | --- | --- | --- | --- | --- |
|  | 1 | 2 | 3 | 1 | 2 | 3 |
| Lignocellulose raw material | Bagasse | Bagasse | Bagasse | Bagasse | Bagasse | Bagasse |
| Pretreatment | | | | | | |
| Treating method | Milling | Milling | Milling/ addition of base compound | Kraft cooking | Milling | Milling |
| Treating time | 10 h | 10 h | 2 h | 90 min | 2 h | 10 h |
| Step (1) (enzymatic saccharification) | Done | Done | Done | None | None | Done |
| Step (2) | | | | | | |
| Mixing ratio: organic solvent/water | 50/50 | 50/50 | 50/50 | — | 50/50 | 50/50 |
| Organic solvent | Acetone | Acetone | Acetone | — | Acetone | Acetone |
| Heating treatment | 160° C.; 30 min | 160° C.; 30 min | 160° C.; 30 min | — | 160° C.; 30 min | 25° C.; 30 min |
| Acid or base | — | Hydrochloric acid | Hydrochloric acid | — | — | — |
| Step (3) | Filtration/distillation under reduced pressure/water-washing | | | Neutralization/ water-washing | Filtration/distillation under reduced pressure/water-washing | |
| Evaluation results | | | | | | |
| Lignin extraction rate (%) | 65.4 | 85.2 | 77.2 | 63.6 | 9.9 | 27.1 |
| Aldehyde yield rate (%) (index of degree of denaturation) | 33.1 | 20.1 | 22.4 | 8.9 | 19.6 | 21 |

Examples 4 to 6

The same procedure as in Example 1 was repeated except that the mixing ratio of acetone/water in the step (2) was changed to 33/67, 67/33 and 90/10 (mass ratio), respectively, and the reaction pressure was left without any control. The results are shown in Table 2.

Example 7

The same procedure as in Example 1 was repeated except that ethanol was used in place of acetone in the step (2), and the reaction pressure was left without any control. The results are shown in Table 2.

Examples 13 to 15

The same procedure as in Example 1 was repeated except that in the step (2), 60 μL of sulfuric acid (concentration: 1.0 M) (Example 13), 120 μL of hydrochloric acid (concentration: 1.0 M) (Example 14) or 21 mg of p-toluenesulfonic acid monohydrate (Example 15) was added into the solvent and the reaction temperature and reaction pressure were adjusted to 140° C. and 1.0 MPa, respectively, and further the extraction solutions collected in the step (3) were neutralized with 1.0 M sodium hydroxide. The results are shown in Table 2.

Example 16

The same procedure as in Example 1 was repeated except that 10 mg of linoleic acid was added into the solvent in the step (2). The results are shown in Table 2.

Examples 17 to 19

The same procedure as in Example 1 was repeated except that in the step (2), 15 mg of aluminum chloride (Example 17), 4 mg of sodium hydroxide (Example 18) or 25 mg of sodium hydroxide (Example 19) was added into the solvent, and the reaction temperature and reaction pressure were adjusted to 140° C. and 1.0 MPa, respectively, and further the extraction solutions collected in the step (3) were neutralized with 1.0 M hydrochloric acid. The results are shown in Table 2.

Comparative Example 4

The same procedure as in Example 1 was repeated except that the mixed solvent of acetone/water used in the step (2) was replaced with acetone ([organic solvent/water](mass ratio): 100/0) and the reaction pressure was left without any control, and further the obtained residue was washed with acetone and water in the step (3). The results are shown in Table 2.

Comparative Example 5

The same procedure as in Example 1 was repeated except that the mixed solvent of acetone/water used in the step (2) was replaced with ethanol ([organic solvent/water](mass ratio): 100/0) and the reaction pressure was left without any control, and further the obtained residue was washed with ethanol and water in the step (3). The results are shown in Table 2.

Comparative Example 6

The same procedure as in Example 1 was repeated except that the mixed solvent of acetone/water used in the step (2) was replaced with water ([organic solvent/water](mass ratio): 0/100) and the reaction pressure was left without any control, and further the obtained residue was washed with acetone and water in the step (3). The results are shown in Table 2.

Comparative Examples 7 and 8

The same procedure as in Example 1 was repeated except that the acetone used in the step (2) was replaced with 1,2-dichloroethane (Comparative Example 7) or ethyl acetate (Comparative Example 8) which both had a solubility in 20° C. water of less than 90 g/L, and the reaction pressure was left without any control. The results are shown in Table 2.

TABLE 2

| | Step (2)*1 | | | | Evaluation results | |
|---|---|---|---|---|---|---|
| | Organic solvent | Mixing ratio: organic solvent/water | Heat treatment | Acid/base | Lignin extraction rate (%) | Weight-average molecular weight |
| Example 1 | Acetone | 50/50 | 160° C.; 30 min | — | 65.4 | 22,014 |
| 2 | Acetone | 50/50 | 160° C.; 30 min | Hydrochloric acid | 85.2 | 3,380 |
| 3 | Acetone | 50/50 | 160° C.; 30 min | Hydrochloric acid | 77.2 | 3,402 |
| 4 | Acetone | 33/67 | 160° C.; 30 min | — | 64.1 | 15,151 |
| 5 | Acetone | 67/33 | 160° C.; 30 min | — | 57.7 | 14,496 |
| 6 | Acetone | 90/10 | 160° C.; 30 min | — | 44.2 | 5,187 |
| 7 | Ethanol | 50/50 | 160° C.; 30 min | — | 51.8 | 10,806 |
| 8 | Ethanol | 67/33 | 160° C.; 30 min | — | 48.0 | 11,574 |
| 9 | Acetonitrile | 50/50 | 160° C.; 30 min | — | 66.7 | 13,700 |
| 10 | Methyl ethyl ketone | 50/50 | 160° C.; 30 min | — | 67.7 | 8,240 |
| 11 | 1,4-Dioxane | 50/50 | 160° C.; 30 min | — | 70.6 | 21,356 |
| 12 | Isopropanol | 50/50 | 160° C.; 30 min | — | 61.5 | 8,893 |
| 13 | Acetone | 50/50 | 140° C.; 30 min | Sulfuric acid | 77.8 | 8,788 |
| 14 | Acetone | 50/50 | 140° C.; 30 min | Hydrochloric acid | 83.7 | 6,618 |
| 15 | Acetone | 50/50 | 140° C.; 30 min | p-Toluenesulfonic acid | 74.9 | 9,551 |
| 16 | Acetone | 50/50 | 160° C.; 30 min | Linoleic acid | 74.4 | 23,866 |
| 17 | Acetone | 50/50 | 140° C.; 30 min | Aluminum chloride | 84.7 | 4,028 |
| 18 | Acetone | 50/50 | 140° C.; 30 min | Sodium hydroxide | 75.5 | 33,973 |
| 19 | Acetone | 50/50 | 140° C.; 30 min | Sodium hydroxide | 82.5 | 32,162 |
| Comparative Example 4 | Acetone | 100/0 | 160° C.; 30 min | — | 21.5 | 3,620 |
| 5 | Ethanol | 100/0 | 160° C.; 30 min | — | 5.5 | 3,413 |
| 6 | — | 0/100 | 160° C.; 30 min | — | 18.2 | 3,941 |
| 7 | 1,2-Dichloroethane*2 | 50/50 | 160° C.; 30 min | — | 11.0 | 1,424 |
| 8 | Ethyl acetate*2 | 50/50 | 160° C.; 30 min | — | 21.0 | 2,691 |

Note
*1In the above Examples and Comparative Examples, bagasse was commonly used as the lignocellulose raw material, and the step (1) and the step (3) were commonly conducted by an enzymatic saccharification treatment and a filtration/distillation under reduced pressure/water-washing treatment, respectively.
*2These organic solvents had a solubility in 20° C. water of less than 90 g/L.

From Table 1, it was confirmed that in Examples 1 to 3 according to the present invention, the lignin degradation products having a low degree of denaturation were produced with a high yield as compared to those lignin degradation products obtained in Comparative Example 1 in which the conventional Kraft cooking method was used, Comparative Example 2 in which no step (1) was conducted, and Comparative Example 3 in which no heat treatment was conducted in the step (2).

From Table 2, it was confirmed that in Examples 1 to 19 according to the present invention, the lignin degradation products were produced with a high yield as compared to those lignin degradation products obtained in Comparative Examples 4 to 6 in which water only or the organic solvent only was used as the solvent in the step (2), and Comparative Examples 7 and 8 in which the solvent having a low solubility in water was used.

Also, as a result of evaluating a solubility in solvents of the lignin degradation products obtained in Examples 1 to 19, it was confirmed that the lignin degradation products obtained in Examples 1 to 17 were uniformly dissolved in the solvents, whereas in Examples 18 and 19, the majority of the obtained lignin degradation products were dissolved in the solvents though a small part of the lignin degradation products still remained insoluble.

Example 20

The same procedure as in Example 3 was repeated except that 20 mol % of hydroquinone (amount added on the basis of the number of moles of lignin calculated by dividing a content of lignin in the substrate by 182 as a molecular weight of a constitutional monomer; hereinafter defined in the same way) as a radical scavenger was added to the solvent in the step (2). The results are shown in Table 3.

Example 21

The same procedure as in Example 3 was repeated except that 40 mol % of hydroquinone as a radical scavenger was added to the solvent in the step (2). The results are shown in Table 3.

Examples 22 to 26

The same procedure as in Example 3 was repeated except that 20 mol % of benzoquinone (Example 22), methoquinone (hydroquinone monomethyl ether) (Example 23), 2,6-di-tert-butyl-4-methyl phenol (Example 24), phenol (Example 25) or ascorbic acid (Example 26) as a radical scavenger was added to the solvent in the step (2). The results are shown in Table 3.

TABLE 3

| | Examples | | | | | | | |
|---|---|---|---|---|---|---|---|---|
| | 3 | 20 | 21 | 22 | 23 | 24 | 25 | 26 |
| Lignocellulose raw material Pretreatment | Bagasse | Bagasse | Bagasse | Bagasse | Bagasse | Bagasse | Bagasse | Bagasse |
| Treating method | Milling/ addition of base compound | Milling/ addition of base compound | Milling/ addition of base compound | Milling/ addition of base compound | Milling/ addition of base compound | Milling/ addition of base compound | Milling/ addition of base compound | Milling/ addition of base compound |
| Treating time | 2 h | 2 h | 2 h | 2 h | 2 h | 2 h | 2 h | 2 h |
| Step (1) (enzymatic saccharification) | Done | Done | Done | Done | Done | Done | Done | Done |
| Step (2) | | | | | | | | |
| Mixing ratio: organic solvent/water | 50/50 | 50/50 | 50/50 | 50/50 | 50/50 | 50/50 | 50/50 | 50/50 |
| Organic solvent | Acetone | Acetone | Acetone | Acetone | Acetone | Acetone | Acetone | Acetone |
| Heating treatment | 160° C.; 30 min | 160° C.; 30 min | 160° C.; 30 min | 160° C.; 30 min | 160°c; 30 min | 160° C.; 30 min | 160° C.; 30 min | 160° C.; 30 min |
| Acid or base | Hydrochloric acid | Hydrochloric acid | Hydrochloric acid | Hydrochloric acid | Hydrochloric acid | Hydrochloric acid | Hydrochloric acid | Hydrochloric acid |
| Radical scavenger | None | Hydroquinone | Hydroquinone | Benzoquinone | Methoquinone | 2,6-Di-tert-butyl-4-methyl phenol | Phenol | L-ascorbic acid |
| Amount of radical scavenger added (mol %)*[1] | — | 20 | 40 | 20 | 20 | 20 | 20 | 20 |
| Step (3) | Filtration/distillation under reduced pressure/water-washing | | | | | | | |
| Evaluation results | | | | | | | | |
| Lignin extraction rate (%) | 77.2 | 89.3 | 96.9 | 95.3 | 92.6 | 93.2 | 94.0 | 82.2 |
| Aldehyde yield rate (%) (index of degree of denaturation) | 22.4 | 15.6 | 16.1 | 18.0 | 14.2 | 11.8 | 16.2 | 12.4 |
| Weight-average molecular weight | 3,402 | 3,094 | 2,571 | 2,771 | 3,086 | 3,459 | 3,425 | 4,050 |

Note
*[1] Amount (mol %) of the radical scavenger on the basis of the number of moles of lignin which is calculated by dividing a content of lignin in the saccharification residue by 180.22 as a molecular weight of an assumed constitutional monomer.

From Table 3, it was confirmed that in Examples 20 to 26 in which the radical scavenger was used in the step (2), the resulting lignin degradation products were produced with a higher yield as compared to the lignin degradation product obtained in Example 3 in which no radical scavenger was used.

Example 27

The same procedure as in Example 2 was repeated except that the following pretreatment and step (1) were conducted, and the resulting saccharification residue was subjected to the step (2). The results are shown in Table 4.

(Pretreatment)

Bagasse as a lignocellulose raw material was charged into a single-screw grinder ("SSC-12040" (Model No.) available from Kinki Industrial Co., Ltd.), and subjected to milling treatment, thereby obtaining a milled bagasse. The resulting milled bagasse was allowed to pass through a sieve (mesh size: 1.18 mm), and the fraction passed therethrough was subjected to the following hydrothermal treatment.

The milled bagasse (absolute dry mass: 1000 mg) was charged into a reaction vessel (capacity: 20 mL), and water was added thereto to adjust an amount of water therein to 19 g. Then, the reaction vessel was hermetically closed, and the contents of the reaction vessel were subjected to microwave heating (hydrothermal treatment) at 140° C. under 0.5 MPa for 2 min while stirring at 900 rpm using a microwave heater "Initiator 60" (available from Biotage Japan Ltd.), thereby obtaining a hydrothermal treatment solution.

[Step (1)]

After the above hydrothermal treatment solution was cooled to 50° C., 2.25 mL of a 1.0 M acetic acid buffer solution (pH: 5.0) was charged into the reaction vessel, and then 2704 of a cellulose/hemicellulase preparation ("Cellic CTec 2") available from Novozymes was added thereto. The resulting mixture was held at 50° C. and subjected to enzymatic saccharification while stirring at 150 rpm. After 48 h, the reaction was terminated, and the resulting reaction solution was subjected to centrifugal separation to separate the solution into a supernatant solution and a saccharification residue. The saccharification residue was subjected to repeated washing and centrifugal separation steps and then to freeze-drying. The content of lignin in the saccharification residue was measured by the above method.

Example 28

The same procedure as in Example 27 was repeated except that in the pretreatment, the reaction temperature and the reaction pressure upon the hydrothermal treatment were controlled to 180° C. and 1.7 MPa, respectively. The results are shown in Table 4.

Example 29

The same procedure as in Example 28 was repeated except that in the pretreatment, the reaction time upon the hydrothermal treatment was controlled to 20 min. The results are shown in Table 4.

Example 30

The same procedure as in Example 28 was repeated except that in the pretreatment, 53 μL of hydrochloric acid (concentration: 1.0 M) was added to the solvent used upon the hydrothermal treatment, and the reaction temperature, the reaction pressure and the reaction time used for conducting the hydrothermal treatment were controlled to 180° C., 1.7 MPa and 2 min, respectively, and in the step (1), after the resulting reaction solution was cooled and neutralized with 1.0 M sodium hydroxide, a 1.0 M acetic acid buffer solution and a cellulose/hemicellulase preparation were added to the obtained solution. The results are shown in Table 4.

TABLE 4

| | Examples | | | | |
|---|---|---|---|---|---|
| | 3 | 27 | 28 | 29 | 30 |
| Lignocellulose raw material | Bagasse | Bagasse | Bagasse | Bagasse | Bagasse |
| Pretreatment | | | | | |
| Treating method | Milling/addition of base compound | Hydrothermal/ 140° C. | Hydrothermal/ 180° C. | Hydrothermal/ 180° C. | Hydrothermal/ 180° C., Addition of hydrochloric acid |
| Treating time | 2 h | 2 min | 2 min | 20 min | 2 min |
| Step (1) (enzymatic saccharification) | Done | Done | Done | Done | Done |
| Step (2) | | | | | |
| Mixing ratio: organic solvent/water | 50/50 | 50/50 | 50/50 | 50/50 | 50/50 |
| Organic solvent | Acetone | Acetone | Acetone | Acetone | Acetone |
| Heating treatment | 160° C.; 30 min | 160° C.; 30 min | 160° C.; 30 min | 160° C.; 30 min | 160° C.; 30 min |
| Acid or base | Hydrochloric acid | Hydrochloric acid | Hydrochloric acid | Hydrochloric acid | Hydrochloric acid |
| Step (3) | | Filtration/distillation under reduced pressure/water-washing | | | |
| Evaluation results | | | | | |
| Lignin extraction rate (%) | 77.2 | 85.8 | 85.1 | 79.0 | 84.8 |
| Aldehyde yield rate (%) (index of degree of denaturation) | 22.4 | 16.4 | 14.6 | 12.5 | 13.3 |

TABLE 4-continued

| | Examples | | | | |
|---|---|---|---|---|---|
| | 3 | 27 | 28 | 29 | 30 |
| Weight-average molecular weight | 3,402 | 2,918 | 3,130 | 3,609 | 3,094 |

From Table 4, it was confirmed that in Examples 27 to 30 in which the hydrothermal treatment was conducted in the pretreatment, the lignin degradation products were produced with a higher yield as compared to that obtained in Example 3 in which no hydrothermal treatment was conducted.

INDUSTRIAL APPLICABILITY

According to the production process of the present invention, it is possible to produce a lignin degradation product having a low degree of denaturation and a high solubility in solvents with a high yield. The lignin degradation product is capable of being easily converted into a low-molecular aromatic compound, and therefore can be suitably used in the application fields, for example, such as agriculture, perfumes and cosmetics, functional resins, dispersants for cements, batteries, etc.

The invention claimed is:

1. A process for producing a lignin degradation product, comprising the following steps (1) to (3):
   Step (1): subjecting a lignocellulose raw material to enzymatic saccharification treatment to obtain a saccharification residue;
   Step (2): subjecting the saccharification residue obtained in the step (1) to heat treatment in a mixed solvent containing water and an organic solvent having a solubility in 20° C. water of not less than 90 g/L to obtain a heat treatment solution containing the lignin degradation product; and
   Step (3): subjecting the heat treatment solution obtained in the step (2) to solid-liquid separation to remove insoluble components from the heat treatment solution, thereby obtaining the lignin degradation product; wherein the enzyme is at least one enzymes selected from the group consisting of cellobiohydrolase, β-glucosidase, endoglucanase and hemicellulase.

2. The process for producing a lignin degradation product according to claim 1, wherein a ratio of the organic solvent to water [organic solvent/water] (mass ratio) in the mixed solvent is from 90/10 to 10/90.

3. The process for producing a lignin degradation product according to claim 1, wherein an SP (solubility parameter) value of the organic solvent is from 8 to 23.

4. The process for producing a lignin degradation product according to claim 1, wherein the organic solvent is at least one compound selected from the group consisting of alcohols, nitriles, ethers and ketones.

5. The process for producing a lignin degradation product according to claim 1, wherein the mixed solvent further comprises an acid or a base.

6. The process for producing a lignin degradation product according to claim 1, wherein the mixed solvent further comprises a radical scavenger.

7. The process for producing a lignin degradation product according to claim 6, wherein the radical scavenger is at least one radical scavenger selected from the group consisting of an aromatic radical scavenger, an amine-based radical scavenger, a stabilized free radical-based radical scavenger, an organic acid-based radical scavenger, a catechin-based radical scavenger and a molecular hydrogen.

8. The process for producing a lignin degradation product according to claim 6, wherein a content of the radical scavenger in the mixed solvent is from 5 to 1000 mol % on the basis of number of moles of lignin in the saccharification residue.

9. The process for producing a lignin degradation product according to claim 1, wherein the mixed solvent is used in an amount being from 2 to 40 times a mass of a solid component in the saccharification residue.

10. The process for producing a lignin degradation product according claim 1, wherein a temperature of the heat treatment in the step (2) is from 40 to 300° C.

11. The process for producing a lignin degradation product according to claim 1, wherein the lignocellulose raw material is subjected to a milling treatment or a hydrothermal treatment as a pretreatment prior to the enzymatic saccharification treatment.

12. The process for producing a lignin degradation product according to claim 11, wherein the milling treatment is carried out in the presence of a basic compound.

13. The process for producing a lignin degradation product according to claim 11, wherein a reaction temperature upon the hydrothermal treatment is from 100 to 400° C.

14. The process for producing a lignin degradation product according to claim 1, wherein the lignocellulose raw material is at least one material selected from the group consisting of conifer chips, broadleaf tree chips, bagasse, rice straws, corn stems and leaves, palm empty fruit bunches, chaffs, palm shells, coconut shells, papers and algae.

15. The process for producing a lignin degradation product according to claim 1, wherein a ratio of the organic solvent to water [organic solvent/water] (mass ratio) in the mixed solvent is from 70/30 to 30/70.

16. The process for producing a lignin degradation product according to claim 1, wherein a ratio of the organic solvent to water [organic solvent/water] (mass ratio) in the mixed solvent is from 60/40 to 40/60.

17. The process for producing a lignin degradation product according to claim 1, wherein the organic solvent is at least one compound selected from the group consisting of ethanol, isopropanol and acetone.

18. The process for producing a lignin degradation product according to claim 1, wherein a temperature of the heat treatment in the step (2) is from 120 to 200° C.

19. The process for producing a lignin degradation product according to claim 1, wherein the lignocellulose raw material is bagasse.

* * * * *